United States Patent [19]

Nankai et al.

[11] 4,434,229

[45] Feb. 28, 1984

[54] ENZYME IMMOBILIZATION WITH AN IMMOBILIZING REAGENT IN VAPOR PHASE

[75] Inventors: Shiro Nankai, Neyagawa; Ken-ichi Nakamura; Takashi Iijima, both of Hirakata, all of Japan

[73] Assignee: Matsushita Electric Industrial Co., Ltd., Japan

[21] Appl. No.: 358,791

[22] Filed: Mar. 16, 1982

Related U.S. Application Data

[63] Continuation of Ser. No. 152,149, May 21, 1980, abandoned.

[30] Foreign Application Priority Data

May 21, 1979 [JP] Japan .................................. 54-62472
Sep. 3, 1979 [JP] Japan ................................. 54-112569

[51] Int. Cl.$^3$ ...................... C12N 11/00; C12N 11/14; C12N 11/06; C12M 1/40
[52] U.S. Cl. ................................... 435/174; 435/176; 435/181; 435/288

[58] Field of Search ............... 435/174, 176, 177, 180, 435/181, 288

[56] References Cited

U.S. PATENT DOCUMENTS

| | | | |
|---|---|---|---|
| 3,705,084 | 12/1972 | Reynolds | 435/180 |
| 4,004,979 | 1/1977 | Avrameas et al. | 435/176 |
| 4,240,889 | 12/1980 | Yoda et al. | 435/180 X |
| 4,251,631 | 2/1981 | Simon | 435/288 X |

*Primary Examiner*—David M. Nafe
*Attorney, Agent, or Firm*—Wenderoth, Lind & Ponack

[57] ABSTRACT

Immobilization of enzymes is carried out by covering the surface of a solid support with an enzyme and then contacting the enzyme with an immobilizing reagent in the vapor phase. The immobilizing reagent is preferably an aldehyde or a polymerized aldehyde. By having the immobilizing reagent in vapor phase, the immobilizing reagent concentration can be easily controlled by the vapor pressure. Additionally, there is obtained a uniform covering of immobilized enzyme on the support, and support surfaces which are uneven or curved can be covered with immobilized enzyme regardless of size.

6 Claims, 7 Drawing Figures

ENZYME IMMOBILIZATION WITH AN IMMOBILIZING REAGENT IN VAPOR PHASE

This is a continuation of Ser. No. 152,149, filed May 21, 1980, now abandoned.

BACKGROUND OF THE INVENTION

The present invention relates to a method of providing enzyme immobilized products which can be continuously and repeatedly used in reactions employing enzymes.

In recent years, the industrial use of specific catalytic reactions of enzymes as sensors and chemical production is performed with the aid of developments in the enzyme immobilizing art. As conventional methods for immobilization of enzymes, there are known a entrapping method of performing immobilization by entrapment within interstitial space of macromolecular matrices, a support bonding method for directly making chemical bond with the immobilizing support, a crosslinking method for crosslinking enzymes with respect to each other, or the like.

Concretely, various organic macromolecules such as resin, sepharose, etc. or inorganic substances such as glass beads, metal, carbon are used as a support for the immobilization of enzymes. The enzyme is immobilized on these supports, using the above-described immobilizing methods. According to the support bonding method, the immobilizing process is complicated and applicable supports are limited. Also, according to the entrapping method, the immobilizing operation is performed by using photo-polymerization or the like to confine the enzyme in the matrices of resin. According to this method, the enzyme activity decline caused by immobilization is small, since the enzyme can be immobilized on the support without chemical modification is inevitably lost through the continuous and repeated use.

According to the crosslinking method, an immobilizing reagent such as glutaraldehyde or the like is used to crosslink the enzymes with respect to each other to immobilize them. Concretely, the surface of the immobilizing support such as glass plate, glass beads, etc. is covered with enzyme solution by spreading, immersing and is dried if necessary. Then, an immobilizing reagent solution such as glutaraldehyde or the like is added to cause the crosslinking reaction thereby to immobilize the enzyme. A several percent dilute solution of glutaraldehyde is generally used. The crosslinking reaction abruptly advances with high immobilizing-reagent concentration whereby the decrease of the enzyme activity is caused. The reaction rate is slow with low immobilizing reagent concentration. During this period, unreacted enzyme is dissolved in the added immobilizing-reagent solution and is lost from the support. This is extremely disadvantageous for promoting the reaction. Therefore, it is almost impossible to uniformly cover the support surface with the membrane of the immobilized enzyme by this method. Since this is a method of applying the immobilizing reagent in as a solution, namely, supplying the immobilizing reagent from a liquid phase when the immobilizing reaction (crosslinking reaction) is performed, the above-described problems are unavoidable.

SUMMARY OF THE INVENTION

Accordingly, an object of the present invention is to provide such a method for immobilization of enzyme which can eliminate disadvantages inherent to the conventional methods.

The present inventors have found a superior immobilizing method which avoids the above-described problems. The characteristics of the enzyme immobilizing method of the present invention are that the immobilizing reaction is caused to be performed while the immobilizing reagents are being supplied from the vapor phase when the immobilizing reagents are applied to immobilize the enzyme. Namely, the immobilizing reagent vaporized and, then, is supplied to the surface of the support coated with an enzyme solution to immobilize the enzyme.

The method of the present invention has many advantages in comparison with the conventional method. First, the process of the immobilizing reaction which exerts a serious influence upon the activity of the immobilized enzyme can be easily controlled. Namely, an advantage is provided in that the immobilizing reagent concentration can be easily controlled by the vapor pressure. Also, according to the present method, the uniform immobilizing enzyme membrane can be easily provided. This is because the immobilizing reagent is supplied from the vapor phase thereby to perform immobilization, under an approximately pre-covered condition, without changing the enzyme concentration on the surface of support for the immobilizing enzyme. Accordingly, the support surface can be covered with the immobilizing enzyme even if the support has an uneven or curved surface etc. or regardless of size.

These and other objects, features, aspects and advantages of the present invention will become more apparent from the following detailed description of the present invention when taken in conjunction with the accompanying drawings.

DESCRIPTION OF THE PREFERRED EMBODIMENT

Figure 1:
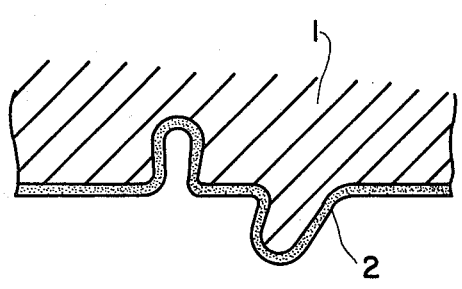
FIG. 1 is a cross-sectional view showing the relationship between the surface shape of enzyme-immobilizing support and the enzyme layer according to the present invention.

FIG. 1 is a cross-sectional view showing one example of a support with enzyme immobilized thereon. Referring to FIG. 1, numeral 1 is an enzyme-immobilizing support, and numeral 2 is a layer including the enzyme. The uneven surface of the immobilizing support 1 is covered in advance with enzyme or an enzyme-containing layer 2. Then, when the immobilizing reagent acts thereupon, the immobilization can be performed with the shape as it is being maintained. Thus, the adhesion between the support and the immobilizing enzyme membrane is also better.

On the other hand, as a method of decreasing the decline of the enzyme activity caused through immobilization, the immobilizing reagent is supplied under conditions where the enzyme substrate or coenzyme in the enzyme requiring the coenzyme are coexistent with the enzyme. This is based on assumption that the coexistence of the enzyme substrate or the coenzyme stabilizes the structure of the enzyme. It is difficult to apply this method to a conventional method for immobilization of enzyme, which supplies the immobilizing reagent from the above-described liquid phase. However, in the method for immobilization of enzyme in accordance with the present invention, the immobilizing operation can be easily performed even when the enzyme substrate or the coenzyme are coexistent. Namely, the immobilizing support is covered with a layer including the enzyme and at least the enzyme substrate or the coenzyme in the enzyme requiring the coenzyme. Then, the immobilizing reaction is performed while the immobilizing reagent is being supplied from the vapor phase thereby to decrease the decline in enzyme activity caused by the immobilizing reaction for the immobilizing operation.

As a method of causing the enzyme to coexist with the enzyme substrate or the coenzyme, they, together with the enzyme, are placed in solution and thereafter the surface of support for immobilizing enzyme is coated. Also, the coexistence can be provided under vapor conditions in a case of the substrate having high vapor pressure such as ethanol or the like in alcohol dehydrogenase.

The several examples of the present invention are presented as follows.

EXAMPLE 1

Figure 2:
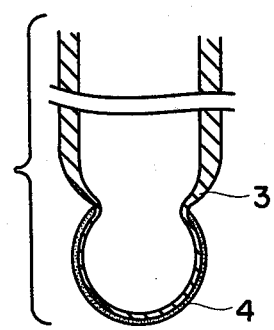
FIG. 2 is a cross-sectional view showing the ion-selective portion of a glass electrode and immobilizing-enzyme membrane covering the ion-selective portion thereof in connection with one embodiment of Example 1 according to the present invention.

FIG. 2 is a cross-sectional view showing an example wherein enzyme 4 is immobilized, by the method of the present invention, to the lower end portion of a glass electrode 3. The ion-selective membrane of the lower end of the glass electrode 3 is coated with immobilized urease. The producing method is as follows.

The urease is used as enzyme 4. The urease is mixed with bovine serum albumin to form a dilute solution. Thereafter, the ion selective portion of the glass electrode 3 is covered with it by a spreading method, etc. Then, after some drying operation, the immobilizing reaction is performed for 60 minutes at 25° C. in glutaraldehyde vapor, so that the sufficiently adhesive immobilized-enzyme membrane is provided. After the reaction completion, it is rinsed in phosphate buffer solution.

Figure 3:
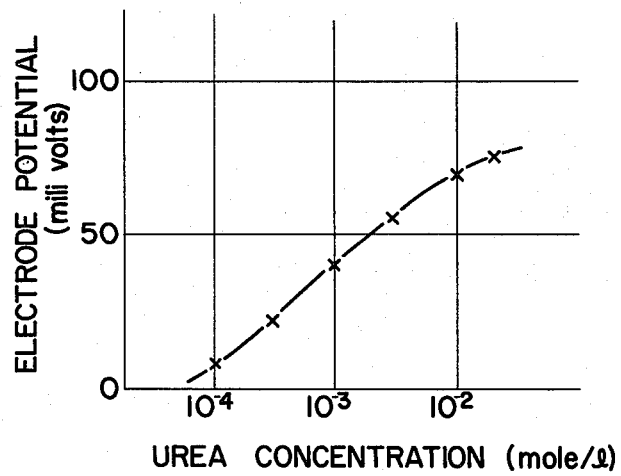
FIG. 3 is a graph showing the relationship between urea concentration and electrode potential in relation to Example 1.
Figure 4:
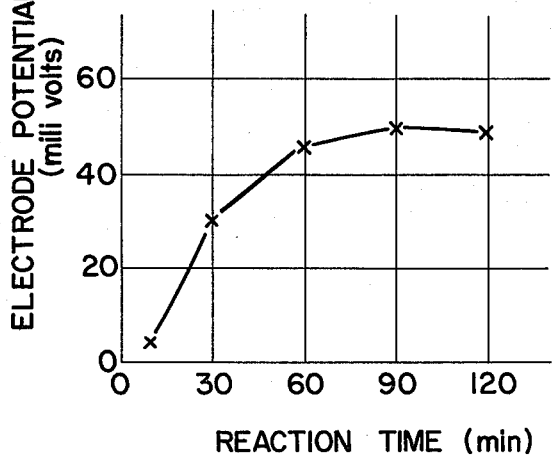
FIG. 4 is a graph showing the relationship between immobilizing reaction time and the electrode potential in relation to Example 1.

According the measurements of variation in electrode potential with respect to urea concentration, in tris buffer solution by the electrode, a superior straight-line relationship was obtained with respect to the logarithmic plot of the urea concentration of $1 \times 10^{-2}$ to $1 \times 10^{-4}$ mole/l as shown in FIG. 3. FIG. 4 shows the relationship between the immobilizing reaction time and the electrode potential with respect to the urea concentration $2 \times 10^{-3}$ mole/l. As apparent from FIG. 4, it is found out that sufficient immobilization is performed because of approximately 60 minutes' immobilizing reaction within the Example 1.

EXAMPLE 2

Figure 5:
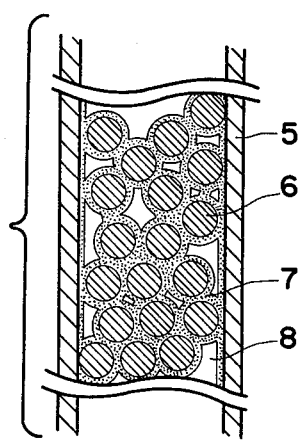
FIG. 5 is a cross-sectional view of an enzyme immobilized column in connection with another embodiment of Example 2 according to the present invention.

Glass beads are filled into a glass column. Then, a dilute solution of α-amylase, as the enzyme flows into the column. Thereafter, air is fed through the column for a drying operation, and the glutaraldehyde vapor is fed at 25° C. for approximately 60 minutes to perform the immobilizing reaction. After the reaction, water is fed for a rinsing operation, so that an α-amylase immobilized column is provided. FIG. 5 is a cross-sectional view showing the immobilized column in connection with an Example 2 of the present invention. Referring to FIG. 5, numeral 5 is a glass column, numeral 6 shows glass beads filling the inside of the column 5, numeral 7 shows enzyme immobilized on the column inner wall and the glass bead surface and numeral 8 shows space portions among the enzyme 7. It was found, in Example 2 that when starch solution, as substrate, in phosphate buffer solution, pH5, was supplied to this column to provide maltose, a sufficient enzyme activity was maintained. In addition, superior properties were provided such as a decrease in the enzyme activity decline caused due to the continuous use, or the like.

EXAMPLE 3

Figure 6:
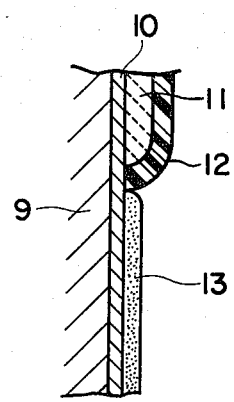
FIG. 6 is a cross-sectional view showing the nesa-membrane of a nesa-glass electrode and the immobilizing-enzyme membrane covering the nesa-membrane thereof in connection with the other embodiment of Example 3 according to the present invention.

FIG. 6 is a cross-sectional view showing one example wherein enzyme is immobilized by the method of the present invention on the surface of a nesa-glass electrode to constitute an enzyme electrode for measurement of substrate concentration. Referring to FIG. 6, numeral 7 is a glass layer, numeral 10 is nesa-layer, numeral 11 is an Ag-paste layer for electric contact and numeral 12 is an epoxy resin layer for insulation. The surface of nesa-layer is coated with immobilized alcohol dehydrogenase 13. The manufacturing method of the enzyme electrode according to an Example 3 of the present invention is as follows.

Phosphate buffer solution wherein alcohol dehydrogenase is dissolved (100 mg/ml), and phosphate buffer solution wherein nicotinamide adenine dinucleotide (NAD) as coenzyme is dissolved (100 mg/ml) are mixed, at the volume ratio of 3:1 with respect to each other. The mixed solution is spread on the surface of the above-described nesa-glass electrode. Then, after a drying operation, the immobilizing reaction is performed, in the glutaraldehyde vapor, at 25° C. for 60 minutes. After the reaction, it is rinsed with the phosphate buffer solution. The immobilized enzyme membrane thus provided was sufficient in adhesive property. This enzyme electrode is referred to as A.

Also, an enzyme electrode was made, under conditions the wherein the coenzyme and the substrate coexist, as described hereinafter. The mixed solution of the enzyme and the coenzyme is applied and spread on the surface of the nesa-glass and is dried as described hereinabove. Then, ethanol is used as the substrate. In the vapor of the ethanol and the glutaraldehyde, the immobilizing reaction is performed at 25° C. for 60 minutes and thereafter it is rinsed. The electrode thus provided is referred to as B.

For comparison with the electrodes A and B, the nesa-glass surface was coated with the enzyme solution only and thereafter the immobilizing reaction was performed in the glutaraldehyde vapor by such a method as described hereinabove. The electrode is referred to as C.

Figure 7:
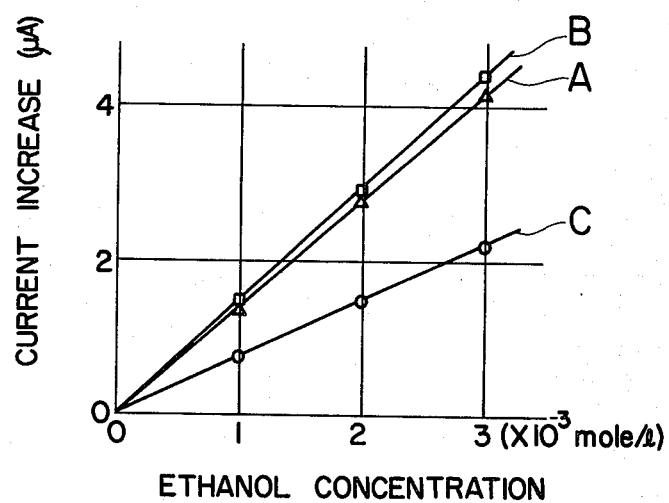
FIG. 7 is a view showing the relationship between the ethanol concentration and the current increase measured with an enzyme electrode in relation to Example 3.

The ethanol concentration is measured, by a method as described hereinafter, with the above-described alcohol dehydrogenase immobilized electrode. The above-described electrode is immersed in the phosphate buffer solution, pH7.0, containing the NAD of $1\times 10^{-3}$ mole/l as the coenzyme. The electrode is set to a constant potential of 0.4 volts vs. a saturated calomel electrode using a potentiostat, and thereafter the ethanol was added to a given concentration. The anodic current of the coenzyme is measured. The current shows a steady state value in about one minute after the pouring of the ethanol. FIG. 7 shows the relationship between ethanol concentration and the current increase portion in connection with the Example 3.

The electrodes A and B provided by the immobilizing method of the present invention are larger in current increase as compared with the electrode C provided by the immobilizing reaction under a condition where the coenzyme and the substrate do not coexist. This is because the enzyme activity decline accompanied by the immobilization is descreased by the coexistence of coenzyme or substrate.

As described hereinabove, according to the method for immobilization of enzyme in accordance with the present invention, the enzyme can be immobilized extremely easily on various supports without chemical modifications.

Also, after the immobilizing reaction has been performed on the glass plate or the like by the present method, reaction products are peeled off to easily provide an immobilized enzyme membrane.

The immobilizing reagent usable according to the method of the present invention is not restricted to glutaraldehyde employed in the examples. Polymerized aldehydes or aldehydes such as 2-hydroxyadipaldehyde crotonaldehyde, acrolein, glyoxal, propionaldehyde, paraformaldehyde could be used. Also, when the surface of the immobilizing support is coated in advance with enzyme, a macromolecular substance which forms the covalent bond through reaction with the immobilizing reagent is mixed with the enzyme and is used, so that the immobilizing operation becomes easier and the enzyme activity decline can be reduced. In addition, the strength of the immobilized enzyme membrane can be increased. Macromolecular substances such as polyethylenimine, polyornithine, polylysine, polyargine, albumin, etc. desirably have functional groups represented by $-NH_2$, $>NH$, $-SH$. The mutual bonds among enzymes, between enzyme and the macromolecular substances or among macromolecular substances advance due to the reaction between these functional groups and the immobilizing reagents, and the reaction between the enzymes and the immobilizing reagents.

Also, when the functional groups exist on the surface of the immobilizing support, a covalent bond can be formed between the support surface and the enzyme and be immobilized by the method of the present invention.

Although the present invention has been described and illustrated in detail, it is to be clearly understood that the same is by way of limitation, the spirit and scope of the present invention being limited only by the terms of the appended claims.

What is claimed is:

1. A method for the immobilization of an enzyme which comprises covering the surface of a solid support with an enzyme and, then immobilizing the enzyme on said support by contacting said enzyme with an immobilizing reagent selected from the group consisting of an aldehyde and a polymerized aldehyde provided in the vapor phase to cause an immobilizing reaction.

2. The method for immobilization of an enzyme in accordance with claim 1, comprising the step of performing the immobilizing reaction under conditions where at least either a substrate for said enzyme or a coenzyme of said enzyme coexists with said enzyme.

3. The method for immobilization of an enzyme in accordance with claim 1 comprising the steps of covering the surface of a support with a mixture of said enzyme and a macromolecular substance, which forms a covalent bond through a reaction with the immobilizing reagent, together with the enzyme.

4. The method according to claim 1 wherein the enzyme is urease, alpha-amylase or alcohol dehydrogenase.

5. The method according to claim 1 wherein the immobilizing agent is 2-hydroxyadipaldehyde, crotonaldehyde, acrolein, glyoxal, propionaldehyde, paraformaldehyde or glutaraldehyde.

6. The method for immobilization of enzyme in accordance with claim 3, wherein said macromolecular substance has at least one functional group selected from the group consisting of: $-NH_2$, $>NH$ or $-SH$.

* * * * *